(12) United States Patent
Van Putten et al.

(10) Patent No.: US 11,079,217 B2
(45) Date of Patent: Aug. 3, 2021

(54) METHODS AND SYSTEMS FOR OPTICALLY CONNECTING AN OPTICAL FIBER SENSOR TO AN OPTICAL SHAPE SENSING CONSOLE

(71) Applicant: KONINKLIJKE PHILIPS N.V., Eindhoven (NL)

(72) Inventors: Elbert Gerjan Van Putten, 's-Hertogenbosch (NL); Martinus Bernardus Van Der Mark, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 456 days.

(21) Appl. No.: 16/088,304

(22) PCT Filed: Apr. 19, 2017

(86) PCT No.: PCT/EP2017/059311
§ 371 (c)(1),
(2) Date: Sep. 25, 2018

(87) PCT Pub. No.: WO2017/182535
PCT Pub. Date: Oct. 26, 2017

(65) Prior Publication Data
US 2020/0300614 A1    Sep. 24, 2020

(30) Foreign Application Priority Data

Apr. 20, 2016 (EP) .................................. 16166110

(51) Int. Cl.
*G01B 11/16* (2006.01)
*A61B 5/06* (2006.01)
*G02B 6/42* (2006.01)
*G01D 5/353* (2006.01)
*G02B 6/02* (2006.01)

(52) U.S. Cl.
CPC ............ *G01B 11/161* (2013.01); *A61B 5/065* (2013.01); *G01D 5/3538* (2013.01);
(Continued)

(58) Field of Classification Search
CPC .............................. G01B 11/161; A61B 5/065
See application file for complete search history.

(56) References Cited

U.S. PATENT DOCUMENTS 7,758,369 B2   7/2010  Miller et al.
8,531,655 B2   9/2013  Klein et al.
(Continued)

FOREIGN PATENT DOCUMENTS

WO   2013076746 A1   5/2013
WO   2015193191 A1   12/2015
WO   2016161245      10/2016

*Primary Examiner* — Charlie Y Peng

(57) ABSTRACT

The present invention relates to a method of and a system for optically connecting an optical fiber sensor (12) to an optical shape sensing console (21). The optical shape sensing console (21) has a number of single optical channels (C1, C2, C3). The optical fiber sensor (12) has a number of single fiber cores (A1, A2, A3) angularly spaced with respect to one another around a longitudinal center axis of the fiber sensor (12) and a fiber sensor connection end (30) for connection to an optical coupler (32; 38) connected to the shape sensing console (21). The optical coupler (32; 38) has the optical channels (C1, C2, C3) arranged for optical connection with the fiber cores (A1, A2, A3). A number of single calibration data sets indicative of individual optical properties of the single fiber cores (A1, A2, A3) is assigned to the single optical channels (C1, C2, C3). The fiber sensor connection end (30) is connected to the optical coupler (32; 38) such that a first fiber core (A2) of the fiber cores (A1, A2, A3) is in optical communication with a first optical channel (C1) of the optical channels (C1, C2, C3). An optical response of the first fiber core (A2) is measured by optically interrogating
(Continued)

the first fiber core (A2) while a first calibration data set of the calibration data sets is assigned to the first optical channel (C1). The first fiber core (A2) is identified among the fiber cores (A1, A2, A3) of the fiber sensor (12) on the basis of the measured optical response of the first fiber core (A2) and the calibration data sets of the fiber sensor (12). If the first fiber core (A2) is identified as not matching with the first calibration data set used hi measuring the optical response, then a second calibration data set of the calibration data sets, which matches with the identified first fiber core (A2), is reassigned to the first optical channel (C1), or the fiber sensor connection end (30) and/or the optical coupler (32; 38) are repositioned such that a second fiber core (A1) matching with the first calibration data set is in optical communication with the first optical channel (C1).

15 Claims, 6 Drawing Sheets

(52) U.S. Cl.
CPC ....... *G02B 6/02042* (2013.01); *G02B 6/4225* (2013.01); *G02B 6/4227* (2013.01)

(56) References Cited

U.S. PATENT DOCUMENTS

| | | | |
|---|---|---|---|
| 8,773,650 | B2 | 7/2014 | Okita et al. |
| 9,820,632 | B2 | 11/2017 | Eberle |
| 10,416,391 | B2* | 9/2019 | Froggatt ............... G01B 11/272 |
| 10,551,170 | B2* | 2/2020 | 'T Hooft ................ G01B 11/24 |
| 10,663,290 | B1* | 5/2020 | Tongue ............... G01B 11/2441 |
| 10,775,157 | B2* | 9/2020 | Gifford ............... G01D 5/35387 |
| 2011/0113852 | A1* | 5/2011 | Prisco .................... G01B 11/18 73/1.15 |
| 2011/0221601 | A1 | 9/2011 | Aguren |
| 2012/0069347 | A1 | 3/2012 | Klein et al. |
| 2013/0158512 | A1 | 6/2013 | Gutierrez et al. |

* cited by examiner

METHODS AND SYSTEMS FOR OPTICALLY CONNECTING AN OPTICAL FIBER SENSOR TO AN OPTICAL SHAPE SENSING CONSOLE

CROSS-REFERENCE TO PRIOR APPLICATIONS

This application is the U.S. National Phase application under 35 U.S.C. § 371 of International Application Serial No. PCT/EP2017/059311, filed on Apr. 19, 2017, which claims the benefit of European Patent Application No. 16166110.3, filed on Apr. 20, 2016. This application is hereby incorporated by reference herein.

FIELD OF THE INVENTION

The present invention generally relates to the field of optical shape sensing. In particular, the present invention relates to a method of and a system for optically connecting an optical fiber sensor to an optical shape sensing console, the optical shape sensing console having a number of single optical channels, the optical fiber sensor having a number of single fiber cores angularly spaced with respect to one another around a longitudinal center axis of the fiber sensor and a fiber sensor connection end for connection to an optical coupler connected to the shape sensing console.

BACKGROUND OF THE INVENTION

A method and system mentioned above can be used in optical shape sensing of elongated interventional devices, in particular in medical or surgical applications. While the present description refers to the use of optical shape sensing in the medical or surgical field, it is to be understood that the invention is not limited thereto.

In the medical field, there is a clear and ongoing trend to replace conventional surgical procedures with minimally invasive interventions. In these interventions, medical devices such as e.g. guidewires, catheters, endoscopes and needles are inserted into the body through small incisions thereby minimizing scarring and reducing complications and side effects for the patient. Physicians can use several visualization techniques to navigate these medical devices inside the body.

In many procedures, X-ray imaging is currently the golden standard to provide real-time monitoring of the devices. However, this imaging technique exposes the patient and the medical team to harmful ionizing radiation. Furthermore, it provides a solely two-dimensional projection. This projection lacks critical information about the three-dimensional shape of the medical instrument such as its direction and orientation with respect to the anatomy of the patient. Additional information about the shape of a device would help the physician tremendously in navigating through the body and could reduce procedure times.

There are several non-imaging tracking technologies that can determine the position and the orientation of devices. Such tracking systems can be based on sensing with electromagnetic, acoustic, impedance, and optical technologies and may use principles such as signal strength (and attenuation), signal phase/frequency shifts, and/or time-of-flight to triangulate a sensor in three-dimensional space.

Optical Shape Sensing (OSS) is one of these tracking technologies. With OSS, a three-dimensional shape of a device can be reconstructed. In OSS, geometrical changes of the device are encoded into the light field that propagates through an optical fiber integrated in the device. Optical interrogation of this optical fiber gives the information needed to, in principle, reconstruct the three-dimensional shape of the whole optical fiber, and hence that of the device, in real-time. Given an appropriate reference frame, one now knows the exact orientation and position of the complete device in real-time.

The optical fiber that is being used to determine the shape of the device contains multiple optical fiber cores, in particular a central core and multiple outer cores that spiral around the central core along the length of the optical fiber. All cores of the sensor have in practice slightly different optical properties due to manufacturing tolerances. Therefore, the fiber cores are calibrated independently in the factory, and this calibration data are made available to the shape sensing system with which the device is to be connected. To this end, either the calibration data are carried along with the device into which the optical fiber is integrated or the calibration are sent in a different way, e.g. through a network.

In use of the optical fiber sensor in optical shape sensing, the fiber cores of the optical fiber sensor are interrogated independently of one another. The fiber cores are in communication with optical channels of an optical shape sensing console in a one-to-one relationship. Each of the optical channels is assigned a calibration data set of one of the fiber cores in preset manner. Thus, it is important for proper shape sensing the optical fiber sensor that upon connection of the optical fiber sensor to the shape sensing console, the "correct" fiber core is in optical communication with the "correct" optical channel. When connecting the connection end of the optical fiber sensor to an optical coupler connected to a shape sensing console, wherein the optical coupler has the optical channels arranged for optical connection with the fiber cores, care has to be taken that the connection end of the optical fiber sensor is connected to the optical coupler in the correct rotational orientation about the longitudinal center axis of the fiber sensor connection end with respect to the optical coupler. In order to facilitate to find the correct orientation of the connection end of the fiber sensor when connecting it to the optical coupler, the optical coupler and the fiber sensor connection end usually have mating key features. Upon connecting the connection end of the fiber sensor to the optical coupler connected to the shape sensing console, the key features of the optical coupler and the fiber sensor connection end are brought into mating relationship so that the fiber sensor is connected in the correct and fixed standard orientation to the optical shape sensing console. In this standard orientation, the calibration data assigned to the optical channels or networks are correctly assigned to the fiber cores of the sensor; for example: outer core "A" is then always connected to optical channel or network "A", etc.

Using a keyed connector, however, has some drawbacks. When the optical fiber is integrated into a guidewire which is used in medical interventions to steer sheaths and catheters into the right place in the patient, it is often necessary to slide those sheaths or catheters over the proximal end of the guidewire into and out of the patient. On the other hand, the optical fiber integrated into the guidewire has to be optically connected to the optical shape sensing console. As it is common to dispose guidewires and catheters after one time use it is reasonable to establish the optical connection of the optical fiber sensor to the shape sensing console via an optical connector or coupler which allows for a fast and reversible connection. However, conventional optical couplers or connectors having key features have much larger outer dimensions than the outer diameter of a typical guidewire, thereby blocking its backloadability and implicitly restraining the use of OSS to a limited class of devices or a small amount of steps during a surgical procedure.

US 2012/0069347 A1 describes an OSS measurement system including a spun optical fiber having multiple cores. Compensation parameters are determined that compensate for variations between an optimal configuration of the cores in the fiber and an actual configuration of the cores in the fiber. The compensation parameters are stored in a memory for compensating subsequently obtained measurement interferometric pattern data for the fiber.

WO 2015/193191 A1 discloses an optical shape sensing system including an optical fiber having a plurality of optical fiber cores. An optical console system is arranged to perform optical calibration measurements on the fiber cores with one common optical scan wavelength range. For each of the optical fiber cores, a measure of its optical length is calculated based on the results of the calibration measurements. Individual optical scan wavelength ranges for each of the outer cores are then determined according to their individual optical lengths relative to the optical length of the center core, so as to compensate for optical length differences between the plurality of optical fiber cores. Thus, there is a need for an improved method of and system for optically connecting an optical fiber sensor to an optical shape sensing console.

SUMMARY OF THE INVENTION

It is an object of the present invention to provide a method of and a system for optically connecting an optical fiber sensor to an optical shape sensing console which do not require optical connectors or couplers having key features in order to make a proper optical connection of the single fiber cores to the optical channels of the shape sensing console.

It is a further object of the present invention to provide a method of and a system for optically connecting an optical fiber sensor to an optical shape sensing console which do not impose additional costs and/or do not add noticeable extra time for establishing the optical connection.

According to a first aspect of the invention, a method of optically connecting an optical fiber sensor to an optical shape sensing console is provided, the optical shape sensing console having a number of single optical channels, the optical fiber sensor having a number of single fiber cores angularly spaced with respect to one another around a longitudinal center axis of the fiber sensor and a fiber sensor connection end for connection to an optical coupler connected to the shape sensing console, the optical coupler having the optical channels arranged for optical connection with the fiber cores, a number of single calibration data sets indicative of individual optical properties of the single fiber cores being assigned to the single optical channels, the method comprising the steps:

i) connecting the fiber sensor connection end to the optical coupler such that a first fiber core of the fiber cores is in optical communication with a first of the optical channels, ii) measuring an optical response of the first fiber core by optically interrogating the first fiber core while a first calibration data set of the calibration data sets is assigned to the first optical channel, iii) identifying the first fiber core among the fiber cores of the fiber sensor on the basis of the measured optical response of the first fiber core and the calibration data sets of the fiber sensor, and iv) if the first fiber core is identified as not matching with the first calibration data set used in measuring the optical response, then iva) reassigning a second calibration data set of the calibration data sets, which matches with the identified first fiber core, to the first optical channel, or ivb) repositioning the fiber sensor connection end and/or the optical coupler such that a second fiber core matching with the first calibration data set, is in optical communication with the first optical channel.

With the method according to the present invention, an optical connection of an optical fiber sensor to an optical shape sensing console can be established which ensures that the "correct" fiber cores of the fiber sensor are connected to the "correct" optical channels of the shape sensing console without the need for a keyed connector on the fiber sensor. Thus, backloadability of a device into which an optical fiber is integrated, is still possible. A user merely has to make the physical connection of the fiber sensor connection end to the optical coupler connected to the shape sensing console such that at least one fiber core of the fiber cores is in optical communication with one of the optical channels without the need for knowing which of the fiber cores is in optical communication with that optical channel. The paired fiber core/optical channel is optically interrogated to measure an optical response of the fiber core of this pair, while one of the calibration data sets which not necessarily is the calibration data set of the actually interrogated fiber core is used in the measurement. The measured optical response of the fiber core is compared to the other calibration data sets of the fiber sensor by which comparison the first fiber core can be identified or individualized among the fiber cores of the fiber sensor. In case that the fiber core on which the optical response has been measured is identified as not matching with the calibration data set used in measuring the optical response, than the method provides to reassign the "correct" calibration data set to the optical channel the measured fiber core is in optical communication with, or to reposition the fiber sensor connection end and/or the optical coupler such that the "correct" fiber core matching with the calibration data set used in the measuring step, is in optical communication with the optical channel to which the calibration data set used in the measurement is assigned.

The reassigning step is advantageous because it can be carried out fully automatically without any intervention by the user. The reassigning step does not require any repositioning of the fiber sensor connection and/or the optical coupler.

The repositioning step can be carried out manually by the user, but also automatically by a positioning device controlled by the system.

The step of measuring an optical response can be the same as the measurement done by the shape sensing console during conventional shape sensing.

The method according to the invention does not impose additional cost to the system, because hardware and software components already available in a conventional shape sensing system can also be used to carry out the method. The calibration data used in the method are already carried along with the fiber sensor when coming from the factory. The method according to the invention does not require noticeable additional time for making the correct connection of the fiber sensor to the optical shape sensing console, because the method can be carried out by the system without time consuming interventions by the user.

In several embodiments, the optical coupler can be arranged on the shape sensing console itself, or can be arranged on a distal end of a patch cord connecting the fiber sensor to the shape sensing console.

The optical channels arranged in the optical coupler can be fiber cores of a single fiber or a plurality of optical fibers corresponding to the number of fiber cores of the fiber sensor.

The fiber sensor can be a device having an integrated optical fiber or an optical fiber itself. The fiber sensor can be a guidewire with integrated optical fiber, for example.

Preferred embodiments of the invention are defined in the dependent claims.

In some embodiments, step i) comprises positioning the fiber sensor connection end and/or the optical coupler with respect to one another such that each of the fiber cores is in optical communication with one of the optical channels in a one-to-one relationship.

In these embodiments, all of the fiber cores of the fiber sensor are axially aligned with the optical channels at the optical coupler upon making the physical connection. Rotational alignment of the fiber sensor connection end with respect to the optical coupler is only insofar necessary as there is a one-to-one relationship between the fiber cores and the optical channels of the optical coupler. However, upon making the connection, it is not necessary to take care that the fiber cores are connected to the "correct" optical channels, because the correct rotational connection will be accomplished by the further steps of the method as described above. Thus, making the physical connection between the fiber sensor connection end and the optical coupler is facilitated.

In further embodiments, step ii) comprises measuring an optical response of each of the fiber cores by optically interrogating the fiber cores, and step iii) comprises identifying each of the fiber cores among the fiber cores of the fiber sensor.

In this way, all the fiber cores of the fiber sensor may be interrogated simultaneously, and all the fiber cores may be identified simultaneously. Thus, in these embodiments, the method can be carried out very quickly.

In further embodiments, step iva) comprises reassigning the calibration data sets to the optical channels so that the identified fiber cores match with the calibration data sets, or step ivb) comprises repositioning the fiber sensor connection end and/or the optical coupler such that the fiber cores matching with the calibration data sets are in optical communication with the optical channels.

In these embodiments, the reassignment of the calibration data sets to the optical channels for all identified fiber cores can be carried out simultaneously, or the fiber sensor connection end and/or optical coupler repositioning is carried out to properly align the "correct" fiber cores with the "correct" optical channels in a single step, further speeding up the correct connection of the fiber sensor with the optical coupler.

In further embodiments, repositioning the fiber sensor connection end and/or the optical coupler comprises rotating the fiber sensor connection end and/or the optical coupler about a longitudinal axis of the fiber sensor connection end which is parallel to the longitudinal center axis of the fiber sensor, or about the longitudinal center axis of the fiber sensor.

In further preferred embodiments, step i) further comprises optically interrogating the first optical channel and positioning the fiber sensor connection end and/or the optical coupler until a strength of an optical response signal from the first fiber core is maximal.

These embodiments are advantageous in that upon initially physically connecting the fiber sensor connection end to the optical coupler it is even not necessary that one of the fiber cores is already aligned with one of the optical channels. This means that, when initially making the physical connection, complete rotational freedom is present with respect to the rotational orientation of the fiber sensor connection end relative to the optical coupler. Axial alignment of at least one of the fiber cores with an optical channel is achieved by positioning, for example rotating the fiber sensor connection end, while measuring the strength of an optical response signal, and when the strength is maximal, it can be concluded that at least one fiber core is properly axially aligned with an optical channel. It will be appreciated that it is not necessary to know which of the fiber cores is axially aligned with the optical channel, according to the principles of the present invention described herein.

In further preferred embodiments, the method further comprises, in particular after steps iva) or ivb) or in step i), optically interrogating each of the fiber sensor cores and positioning the fiber sensor connection end and/or the optical coupler until a strength of an optical response signal from each of the fiber cores is maximal.

These embodiments provide a fine positional adjustment of the fiber sensor cores so that optical shape sensing can be carried out with optimum signal strength.

In further preferred refinements, the measured optical response in step ii) includes a spatially resolved scattering profile of the first fiber core.

It is advantageous here that the measurement carried out for identifying the fiber core or fiber cores is not different from the measurements done by the shape sensing console during conventional shape sensing. Thus, the functions of the shape sensing console already present in the system can be advantageously used for establishing the correct optical connection of the fiber sensor to the shape sensing console.

It should be noted that the calibration data may have been obtained from reference measurements where the fiber sensor was in a straight shape, without significant twist and curvature, whereas the optical response in step ii) may be measured when the fiber sensor is in a shape that has significantly more curvature than in the reference measurement taken during the calibration. This is a further advantage of the method according to the invention, because the user has not to manipulate the fiber sensor when the measurement is carried out in step ii), for example to shape the fiber sensor in a specific way.

The calibration data sets may include spatially resolved scattering profiles or spatial intensity profiles thereof of the fiber cores, which have been obtained from reference measurements on the fiber cores.

Such reference measurements may have been made in the factory where the fiber sensors are produced, and the calibration data accompany the fiber sensors, for example in an integrated RFID chip. The calibration data sets of a plurality of fiber sensors may be input into a data base in the shape sensing console, and on connecting one of the fiber sensors to the shape sensing console, the shape sensing console may register the fiber sensor ID by reading out the integrated RFID chip, and the shape sensing console can then get the corresponding calibration data sets for the fiber cores of the connected fiber sensor from the database. Alternatively, the calibration data sets of a fiber sensor can be carried along with the device using a USB-stick or something similar. On connecting the device, this USB-stick is then inserted into the interrogation console.

In further preferred embodiments, the fiber cores have fiber Bragg gratings as scattering structures, and step iii) comprises identifying the first fiber core by using a spatial intensity profile obtained from the spatially resolved scattering profile.

In these embodiments, the fiber cores have fiber Bragg gratings written over a part of or over their complete length. Although the gratings in each of the fiber cores should be nominally the same, the manufacturing process can induce small differences between them. Some of these differences, such as shadowing dips or small irregularities in grating strength are visible in the measured spatial intensity profiles, i.e. the absolute values of the spatially resolved scattering profiles of the fiber cores. These differences visible in the reflected spatial intensity profile can be advantageously used for identifying the single fiber cores, because even when the fiber sensor is bent, the spatial intensity profile hardly changes. Therefore it is well suited to identify the fiber cores.

Preferably in the context of the embodiments just mentioned before, step iii) of the method preferably further comprises calculating a cross correlation of the measured optical response with the calibration data sets of the fiber cores.

The cross-correlation of the optical response measured in step ii) with reference measurements from which the calibration data sets were obtained is calculated for identifying the fiber core on which the optical response has been measured in step ii).

In further embodiments, step iii) comprises calculating a twist or curvature in the fiber sensor from the spatially resolved scattering profile and identifying the first fiber core based on oscillations in the calculated twist or curvature.

This embodiment makes use of the sensor geometry of the fiber sensor for identification of the fiber cores. Since the geometry of a sensor is never perfect and small differences between the different cores exist, the reconstruction of the shape of the fiber sensor will show distinct errors, when the calibration data sets are interchanged between the cores. When the calibration data sets of the outer cores are interchanged, and when there is a curvature or twist in the fiber sensor, oscillations will appear on the calculated twist. These oscillations have a frequency corresponding to the twist rate of the fiber sensor and can be detected easily.

In further embodiments, the fiber sensor connection end and/or the optical coupler may have a mark that may help to align the fiber sensor connection end approximately in the right orientation with respect to the optical coupler. Such a mark, however, should not block or restrict backloadability of the device. The advantage of such a mark is that the alignment procedure upon beginning to make the connection may be faster and more robust. The mark may have no significant physical size compared to the size of the connector end and may itself not give perfect alignment, but only provide guidance to a proper alignment. Examples of marks are a thin line of different color or reflection, written on the device with paint, ink or by local alteration of the material by a laser, and/or a magnetic field due to magnetization of the proximal part of the device, for example at right angles to the longitudinal axis of the device.

According to a second aspect of the invention, a system for optically connecting an optical fiber sensor to an optical shape sensing console is provided, the optical shape sensing console having a number of single optical channels, the optical fiber sensor having a number of single fiber cores angularly spaced with respect to one another around a longitudinal center axis of the fiber sensor and a fiber sensor connection end for connection to an optical coupler connected to the shape sensing console, the optical coupler having the optical channels arranged for optical connection with the fiber cores, the system comprising:

a calibration data module configured to have stored a number of single calibration data sets indicative of individual optical properties of the single fiber cores, the calibration data sets being assigned to the single optical channels, a measuring module configured to measure an optical response of a first fiber core of the fiber cores connected to a first optical channel by optically interrogating the first fiber core while a first calibration data set of the calibration data sets is assigned to the first optical channel, an identifying module configured to identify the first fiber core among the fiber cores of the fiber sensor on the basis of the measured optical response of the first fiber core and the calibration data sets of the fiber sensor, the system further comprising at least one of the following:

a) a reassigning module configured to reassign a second calibration data set of the calibration data sets, which matches with the identified first fiber core, to the first optical channel, b) a repositioning module configured to reposition the fiber sensor connection end and/or the optical coupler such that a second fiber core matching with the first calibration data set, is in optical communication with the first optical channel.

The system according to the invention has similar and/or identical advantages as the method according to the invention, and it is to be understood that the system according to the invention has similar and/or identical preferred embodiments as the method according to the invention as defined in the dependent claims of the method.

It is to be understood that the modules of the system mentioned above may be single modules, or one or more of the modules may be configured to carry out the functions of one or more of the other modules. The modules of the system may be embodied as hardware, software and/or firmware.

According to a third aspect of the invention, an optical shape sensing system is provided, comprising:

an optical shape sensing console, the optical shape sensing console having a number of single optical channels, at least one optical fiber sensor having a number of single fiber cores angularly spaced with respect to one another around a longitudinal center axis of the fiber sensor and a fiber sensor connection end, an optical coupler for connecting the optical fiber sensor to the optical shape sensing console, the optical coupler having the optical channels arranged for optical connection with the fiber cores, and a system according to the second aspect.

According to a fourth aspect of the invention, a computer program comprising program code means for causing a computer to carry out the steps of the method according to the first aspect is provided, when said computer program is carried out on a computer.

BRIEF DESCRIPTION OF THE DRAWINGS

These and other aspects of the invention will be apparent from and elucidated with reference to the embodiment(s) described hereinafter with reference to the drawings. In the following drawings.

DETAILED DESCRIPTION OF THE INVENTION

In the following, embodiments of a method of and a system for optically connecting an optical fiber sensor to an optical shape sensing console with a correct mutual assignment of the fiber cores and calibration data used in optical shape sensing. The method and system according to the invention is advantageous in shape reconstruction of an optical fiber sensor in three dimensions. Shape reconstruction using an optical fiber sensor may be performed by an optical shape sensing system, an embodiment of which will be first described with reference to FIG. 1.

As far as not indicated otherwise, an optical fiber sensor can be an optical fiber itself or a device having an optical fiber integrated into the device. Such a device may be, for example a guidewire, a catheter, an endoscope or the like.

Figure 1:
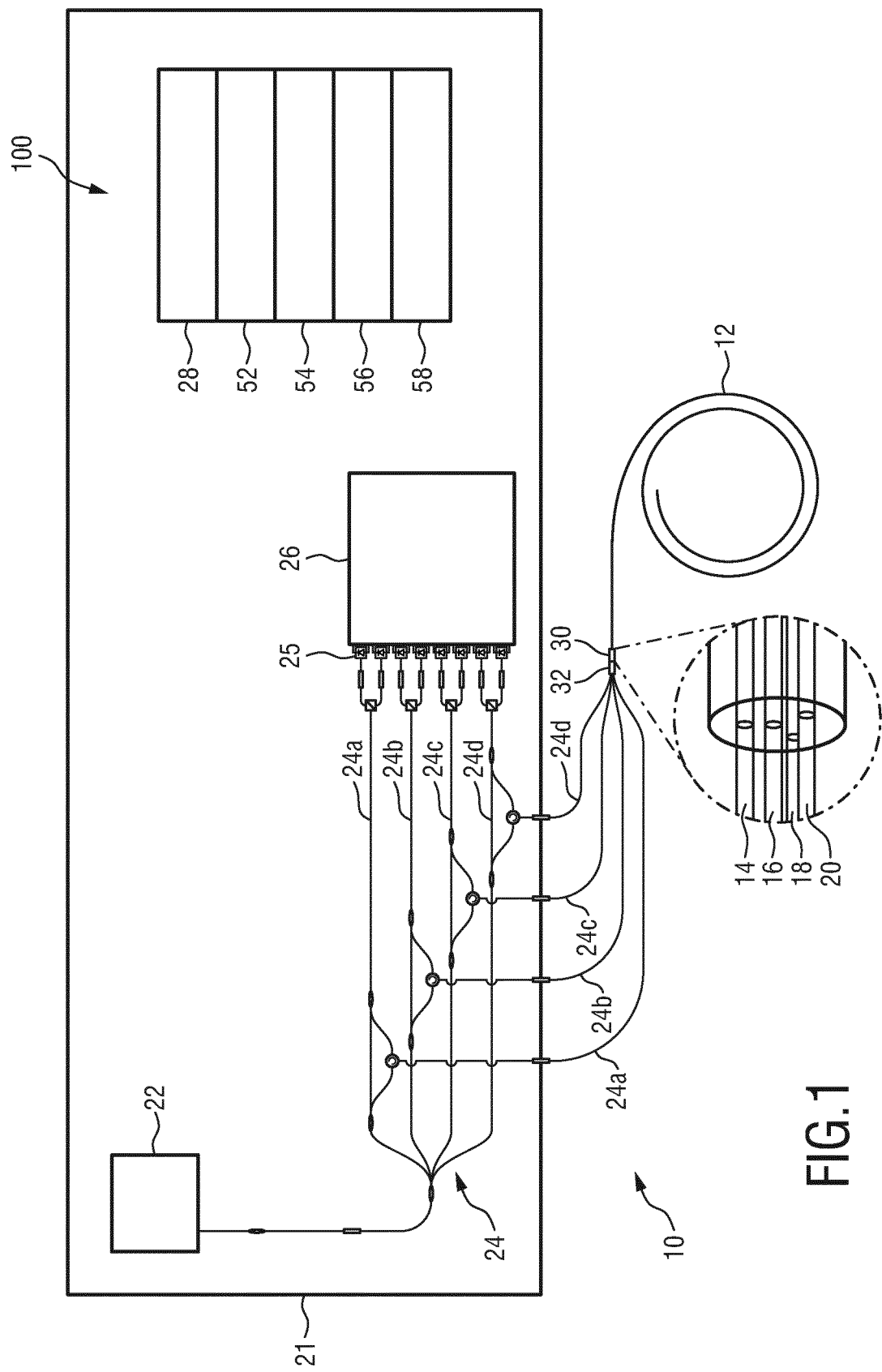
FIG. 1 shows an embodiment of parts of an optical shape sensing system for use in the present invention.
Figure 2:
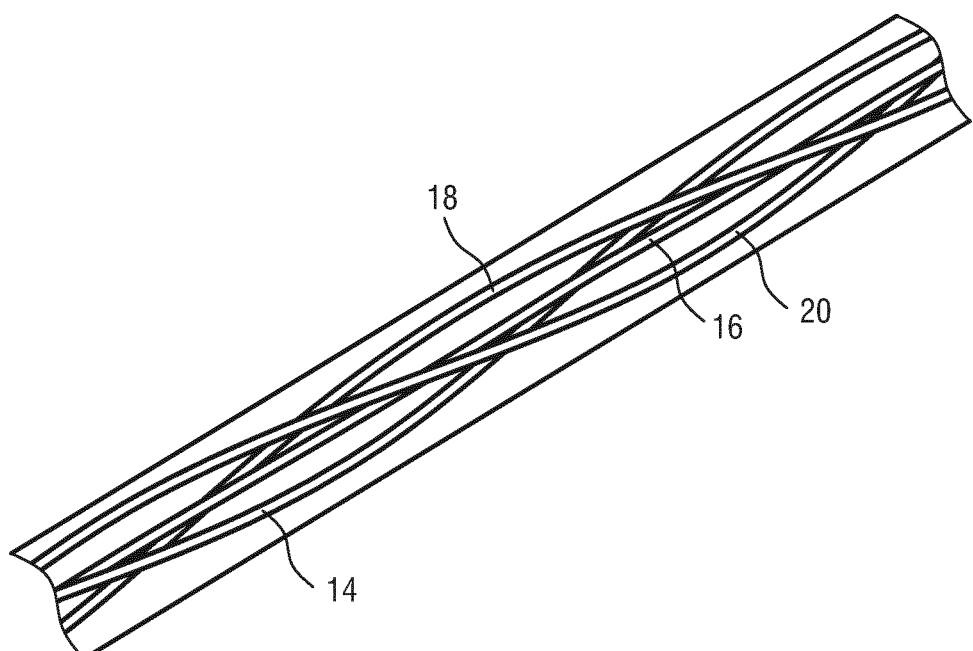
FIG. 2 shows a piece of length of an optical fiber for use in the present invention.

FIG. 1 shows parts of an optical shape sensing system 12 configured as a multi-channel optical frequency domain reflectometry (OFDR)-based distributed-strain sensing system for sensing an optical fiber sensor 12. The optical fiber sensor 12 has a plurality of cores 14, 16, 18, 20, in the present example four cores with one center core 16 and three outer cores 14, 18, 20. FIG. 2 shows a piece of length of the fiber cores 14, 16, 18, 20 with the outer cores 14, 18, 20 spiraled around the center core. The outer cores are angularly spaced with respect to one another around the longitudinal center axis of the fiber sensor 12. The longitudinal center axis coincides with the center core 16. According to a number of four cores in the present example, the angular spacing between neighboring cores is 120°.

With reference again to FIG. 1, the optical shape sensing system 10 comprises a shape sensing console 21. The optical shape sensing console 21 is also referred to herein as interrogator for optically interrogating the fiber sensor 12.

The shape sensing console 21 comprises a tunable light source 22 which can be swept through a range of optical frequencies. The light emitted by the light source 22 is coupled into an optical interferometric network 24 having four optical channels 24a, 24b, 24c, 24d. In use of the optical shape sensing system 10, each of the single fiber cores 14, 16, 18, 20 is connected with one of the optical channels 24a, 24b, 24c, 24d in a one-to-one relationship, as will be described hereinafter in more detail.

When the tunable light source 22 is swept through a range of optical frequencies, each channel 24a, 24b, 24c, 24d, and thus each fiber core 14, 16, 18, 20 of the fiber sensor 12 is simultaneously but independently optically interrogated, and the resulting interference pattern from each of the fiber cores 14, 16, 18, 20 is routed to a processing unit 26 via respective photodetectors 25. Each channel 24a, 24b, 24c, 24d is processed independently from the other channels. The distributed strain measurements recorded using the multiple-channel OFDR system from the cores 14, 16, 18, 20 may then be exported for use for further processing, in particular for three-dimensional shape reconstruction of the fiber sensor 12 and for visual display of the reconstructed three-dimensional sensor fiber shape.

In OSS, geometrical changes of the fiber sensor 12 are encoded into the light field that propagates through the fiber sensor 12. Optical interrogation of the fiber sensor 12 gives the information needed to, in principle, reconstruct the three-dimensional shape of the whole fiber sensor in real-time. Given an appropriate reference frame, it is possible to know the exact orientation and position of the complete fiber sensor in real-time.

For a more detailed overview about the principles of optical shape sensing, reference is made to US 2012/0069347 A1 and U.S. Pat. No. 8,773,650 B2. The whole content of these documents is incorporated herein by reference.

The fiber cores 14, 16, 18, 20 of the fiber sensor have in practice slightly different optical properties. Therefore, the cores 14, 16, 18, 20 are calibrated independently in the factory, and this calibration data is carried along with the fiber sensor 12.

For each fiber sensor 12 used with the optical shape sensing console 21, the calibration data comprises a number of single calibration data sets according to the number of fiber cores the fiber sensor 12 has. One calibration data set is indicative of individual optical properties of one fiber core of the fiber sensor 12. The shape sensing console 21 or the optical shape sensing system 10 may have a calibration data module 28 which is configured to have stored the single calibration data sets. Upon connection of the fiber sensor 12 to the shape sensing console or interrogator 21, the system reads out the calibration data sets assigned to the fiber cores 14, 16, 18, 20 and assigns the calibration data sets to the optical channels 24a, 24b, 24c, 24d in a one-to-one relationship.

Since for proper shape reconstruction the correct calibration data set has to be used for each core, it is important that each fiber core 14, 16, 18, 20 is connected to that optical channel 24a, 24b, 24c, 24d to which the calibration data set of this fiber core is assigned. Therefore, in conventional systems, a fiber sensor is connected to the shape sensing console in a fixed standard orientation in order to ensure the correct assignment of the calibration data sets to the fiber cores. This fixed standard orientation in conventional systems is accomplished by using optical connectors having key features so that a fiber sensor connection end 30 can be connected to an optical coupler 32 or 38 connected to the interrogator 21 only in the fixed standard orientation. This will be described further with reference to FIGS. 3 to 5.

Figure 3:
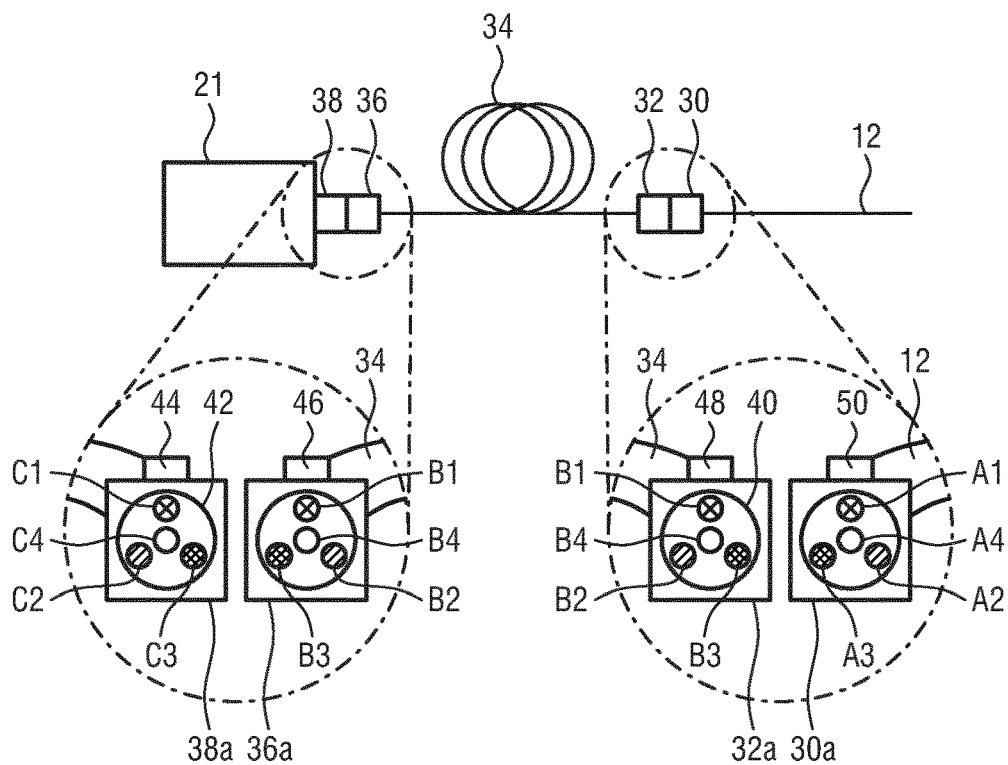
FIG. 3 shows a simplified sketch of an optical shape sensing system with enlarged details thereof.
Figure 4:
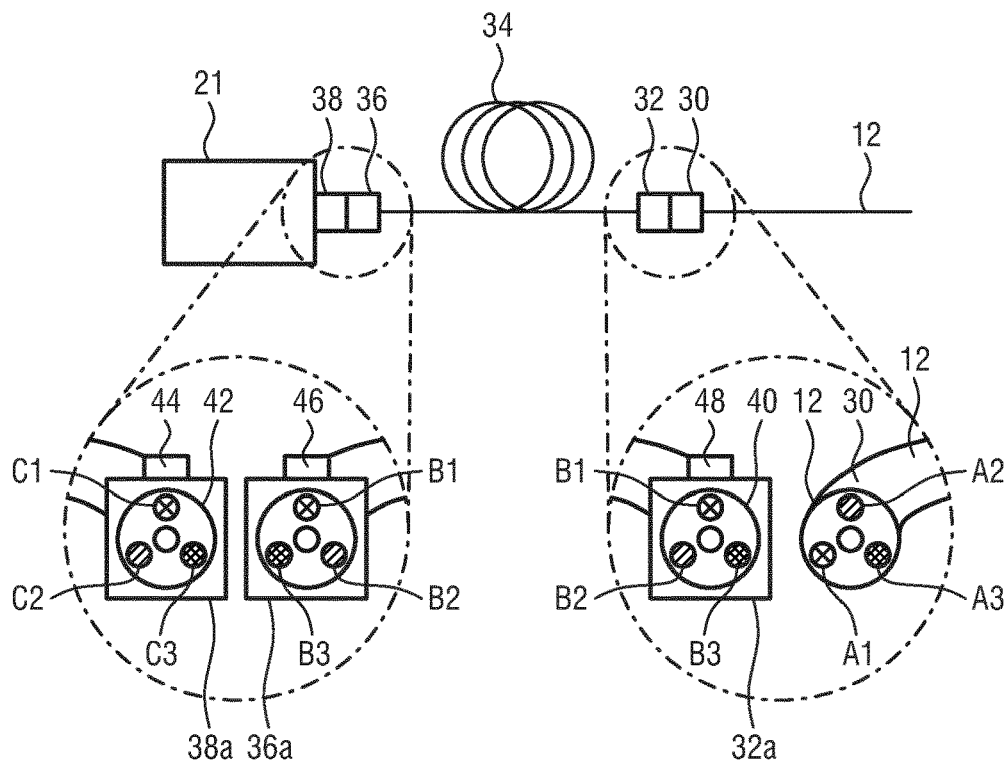
FIG. 4 shows a sketch similar to FIG. 3 of an optical shape sensing system modified with respect to FIG. 3.
Figure 5:
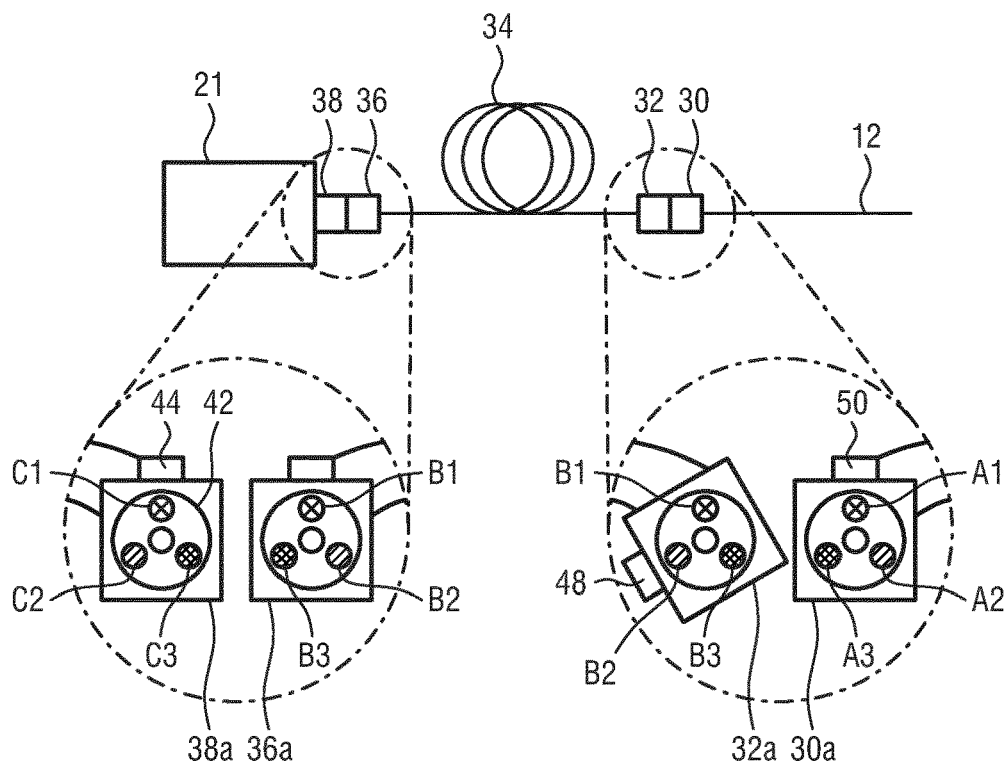
FIG. 5 shows a further sketch similar to FIG. 3 of an optical shape sensing system modified with respect to FIG. 3.

FIGS. 3 to 5 schematically show optical shape sensing systems with those elements corresponding to elements in FIG. 1 being labeled with the same reference numerals as in FIG. 1. As such, FIG. 3 shows a shape sensing console 21 and an optical fiber sensor 12 connected to the shape sensing console 21. The sensor fiber 12 is connected to the shape sensing console 21 via a patch cord 34. The patch cord 34 is not necessarily present, but the sensor fiber 12 can be directly connected to the shape sensing console 21.

The connection end 30 of the sensor fiber 12 is connected to the optical coupler 32 arranged at the distal end of the patch cord 34. The proximal end of the patch cord 34 has a connection end 36 connected to an optical coupler or connector 38 connected to the shape sensing console 21. It is to be understood that the fiber sensor connection end 30 can be directly connected to the coupler 38 when the patch cord 34 is not used.

The connection end 30 of the sensor fiber 12 is configured as a keyed connector 30a in which the proximal end of the fiber sensor 12 terminates with the fiber cores, here labeled with A1, A2, A3, A4 arranged for optical connection with fiber cores B1, B2, B3, B4 of an optical fiber 40 terminating in a keyed connector 32a forming the optical coupler 32 of the patch cord 34 at the distal end of the patch cord 34. The fiber cores A1, A2, A3 of the fiber sensor 12 correspond to the outer fiber cores 14, 18, 20 in FIG. 1, and the fiber core A4 of the fiber sensor 12 corresponds to the central fiber core 16 in FIG. 1.

The proximal connection end 36 of the patch cord 34 has a connector 36a with the fiber cores B1, B2, B3, B4 arranged for optical connection with optical channels C1, C2, C3, C4. The optical channels may be fiber cores of an optical fiber 42 or single one-core fibers terminating in a connector 38a forming the optical coupler 38 connected to the shape sensing console 21. The optical channels C1, C2, C3, C4 correspond to the optical channels 24a, 24b, 24c, 24d in FIG. 1.

The connector 38a has a key 44, and the connector 36a has a key 46. The keys 44 and 46 are configured to mate for locking the connection between the connectors 36a and 38a in a rotationally fixed standard orientation. As can be taken from FIG. 3, the channels C1, C2 and C3 in the connector 38a have the same rotational orientation with respect to the key 44 as the fiber cores B1, B2, B3 with respect to the key 46. Further, connector 32a has a key 48 and the connector 30a has a key 50, wherein the keys 48 and 50 mate for locking the connection between the connectors 30a and 32a in a rotationally fixed standard orientation. Again, the fiber cores A1, A2, A3 of the fiber sensor 12 have the same rotational orientation with respect to the key 50 as the fiber cores B1, B2, B3 at the distal end of the patch cord 34 with respect to the key 48. Thus, by connecting the connector 36a to connector 38a and the connectors 30a to connector 32a, there is no ambiguity in the connections of the fiber cores A1, A2 and A3 with respect to the channels C1, C2, C3, and it is ensured that the fiber cores A1, A2, A3 of the sensor fiber 12 are in correct optical communication with the optical channels of the shape sensing console 21.

However, using connectors having keys has the drawback that such connectors have much larger outer dimensions than the outer diameter of the fiber sensor 12 which may be a guidewire having an optical fiber integrated therein. A typical outer diameter of a guidewire is 0.89 mm. An optical connector having a key arranged at the proximal end of the guidewire would block backloadability thereof, i.e. the connector would it render impossible to slide a sheath or catheter over the guidewire from the proximal end of the guidewire.

Thus, it is desirable to have a solution which does not require a connector like connector 30a having a key 50 at the proximal end of the fiber sensor 12. However, it will be appreciated that proper rotational alignment of the fiber cores A1, A2, A3 of the fiber sensor 12 with respect to the optical channels A1, A2 and A3 of the optical coupler 38 will be difficult without a keyed connector. This situation is shown in FIG. 4, where the connection end 30 of the fiber sensor 12 does not have the connector 30a with the key 50. However, due to the missing key 50, the orientation of the outer cores A1, A2 and A3 inside the fiber sensor 12 is unknown. After a connection has been made between the fiber sensor connection end 30 and the connector 32a, it might therefore happen that the fiber cores A1, A2, A3 are connected to the channels C1, C2, C3 in a wrong relationship. For example, as shown in FIG. 4, outer core A2 of the fiber sensor 12 is connected to fiber core B1 of the patch cord 34 and, consequently, with channel C1 of optical coupler 38. Since the shape sensing console 21 does not "know" that fiber core A2 is connected to channel C1, but "expects" that fiber core A1 is connected to channel C1, the shape sensing console assigns the calibration data set of fiber core A1 to channel C1. Upon conducting a shape sensing measurement on the fiber sensor 12, the fiber core A2 is interrogated using the calibration data set of fiber core A1, and proper three-dimensional reconstruction of the shape of the fiber sensor 12 is impaired.

A similar problem arises when the fiber cores B1, B2, B3 in the connector 36a at the proximal end of the patch cord 34 are angularly orientated with respect to the key 46 differently from the angular orientation of the fiber cores B1, B2, B3 with respect to the key 48 of the connector 32a at the distal end of the patch cord 34, as illustrated in FIG. 5. This means that the orientations of the connectors 36a and 32a are not clocked with respect to each other. As shown in FIG. 5, in connector 32a, outer core B2 is located at the key 48, while in connector 36a outer core B1 is located at the key 46. In this exemplary setup, outer core A1 of the fiber sensor 12 would erroneously connect to channel A2 in the optical coupler 38 and, thus, erroneously connect to the "wrong" optical channel in the interrogator 21.

Thus, it can happen again that the outer cores A1, A2 and A3 of the fiber sensor 12 are connected to the "wrong" optical channel of the optical channels C1, C2, C3, C4 of the interrogator 21, depending on which patch cord 34 is used. Although it is possible to clock the two connectors 32a and 36a of the patch cord 34, this might add additional costs during manufacturing of patch cords and may be therefore undesirable.

The present invention remedies these problems by providing a method and system by which the optical fiber sensor 12 can be connected to the shape sensing console 21 in the proper manner so that the correct calibration data sets are used in shape sensing the fiber sensor 12, without the need for a connector at the proximal end of the fiber sensor 12 having a key which would otherwise block backloadability.

Figure 6:
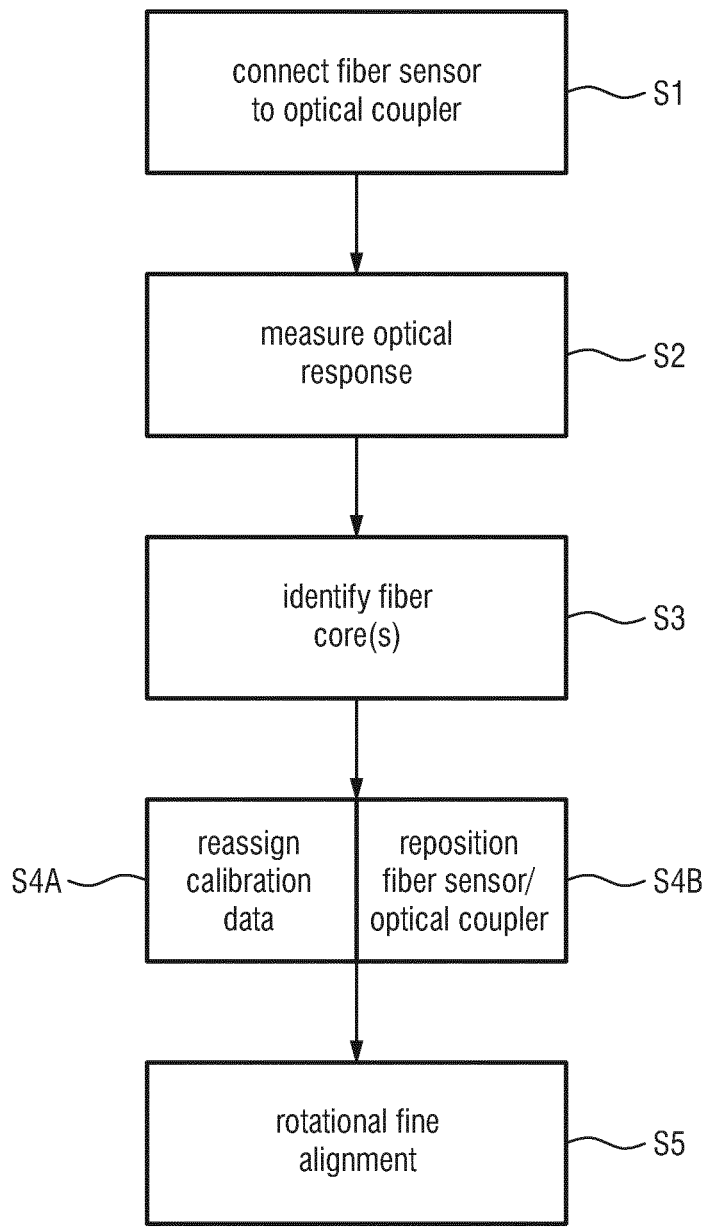
FIG. 6 shows a flow chart of a method of optically connecting an optical fiber sensor to an optical shape sensing console of an optical shape sensing system.

The method of optically connecting the fiber sensor 12 to the interrogator 21 will be described with reference to FIGS. 1, 4 and 6. FIG. 6 shows a flow chart of the method steps. The method to be described below will work when connecting the proximal connection end 30 of the fiber sensor 12 directly to the optical coupler 38 in FIG. 4, or when connecting the fiber sensor 12 to the patch cord 34 as shown in FIG. 4. For the sake of simplicity, the method will be described with reference to the case that the fiber sensor connection end 30 is directly connected to the optical coupler 38. If the patch cord 34 is used, the fiber cores B1, B2, B3 correspond to the optical channels C1, C2, C3.

In step S1 in FIG. 6, the fiber sensor connection end 30 is connected to the optical coupler 38. This connection is a physical connection such that at least one of the outer fiber cores A1, A2 and A3 of the fiber sensor 12 is in optical communication with one of the optical channels C1, C2 and C3 of the optical coupler 38. At this stage of the method it is not necessary that the assignment between the fiber core and the optical channel is correct. For example, assume that fiber core A2 of the fiber sensor 12 is in optical communication with optical channel C1 of the coupler 38 after making the connection, as shown in FIG. 4. Upon making the connection in step S1, the interrogator 21 may read out the calibration data sets of the fiber cores A1, A2, A3 and A4 of the fiber sensor 12 and assigns the calibration data sets to the optical channels C1 (24a), C2 (24b), C3 (24c), C4 (24d) in a one-to-one relationship, however without knowing whether the distribution of the calibration data sets among the optical channels is correct with respect to the fiber cores.

Step S1 can be performed such that all outer fiber cores A1, A2 and A3 are in optical communication with the optical channels C1, C2 and C3 in a one-to-one relationship, but it is principally sufficient that only one of the fiber cores A1, A2 and A3 of the fiber sensor 12 is in optical communication with one of the optical channels C1, C2 and C3.

Assume that at least fiber core A2 of the fiber sensor 12 is in optical communication with one of the optical channels C1, C2 and C3, for example optical channel C1.

In step S2, an optical response of the fiber core A2 is measured by optically interrogating the fiber core A2 which is in optical communication with the optical channel C1 to which, for example, the calibration data set of fiber core A1 was assigned, and this calibration data set has been used in the measurement.

The measurement of the optical response of the fiber core A2 may be performed in a way which is not different from the measurements done by the interrogator 21 during conventional shape sensing. By measuring the optical response of the fiber core A2, a state-file of the fiber core A2 is created which comprises the spatially resolved scattering profile of the core A2, which may be obtained, for example, with distributed sensing techniques such as optical frequency domain reflectometry (OFDR) as described above.

Since the interrogator 21 does not know which of the fiber cores A1, A2 and A3 has been actually interrogated in step S2, the method proceeds to step S3 in FIG. 6, in which the interrogated fiber core, here outer fiber core A2, is identified among the outer fiber cores A1, A2 and A3 of the fiber sensor 12. This identification process uses the measured optical response (state-file) of the interrogated fiber core and the calibration data sets of all of the fiber cores A1, A2 and A3 of the fiber sensor 12.

In the identification process, a comparison is made between the measured state-file and the calibration data sets of the fiber sensor 12. The measured state-file of the interrogated fiber core A2 can be evaluated according to different aspects which can be used to identify the interrogated fiber core and thus the orientation of the fiber sensor 12 with respect to the coupler 38. These aspects will be explained below in more detail.

After identification of the interrogated fiber core, in the present example fiber core A2, the following scenarios can occur.

In a first scenario, the interrogated fiber core is identified as the fiber core to which the calibration data set belongs which has been used in the measuring of the fiber core. In this case, no further action is necessary.

In a different scenario, and as it is the case in the example of FIG. 4, the interrogated fiber core is identified as the fiber core A2 and has been interrogated through the optical channel C1 to which the calibration data set of fiber core A1 were assigned during the measurement. Then, the method proceeds to step S4A or S4B.

In step S4A, the calibration data set of the identified fiber core, in the present example of fiber core A2, is reassigned to the optical channel, here optical channel C1, the interrogated fiber core A2 is in optical communication with so that during the following use of the system in optical shape sensing the correct calibration data set matching with the identified fiber core, here A2, is used for proper shape sensing.

Thus, the proper optical connection between the interrogated fiber core and the optical channel through which the fiber core has been interrogated, is established by a reassignment of the calibration data set of the interrogated fiber core to that optical channel. A repositioning of the fiber sensor connection end 30 with respect to the coupler 38 is then not necessary.

In another embodiment, the fiber sensor connection end 30 and/or the coupler 38 is repositioned relative to the other such that the fiber core, here A1, which matches with the calibration data set used in the interrogation, is brought into optical communication with the optical channel, here C1, through which the fiber core has been interrogated. In the present example, the fiber sensor connection end 30 may be rotated about the longitudinal center axis of the fiber sensor 12 such that fiber core A1 is brought into optical communication with optical channel C1 through which previously the fiber core A2 has been interrogated.

Steps S4A and S4B can be combined, if appropriate. Step S4B can be carried out manually or by an actuator (not shown) configured to drive the connection end 30 and/or the coupler 38 and controlled by the shape sensing console 21.

In further embodiments, step S1 in FIG. 6 may comprise positioning the fiber sensor connection end 30 and/or the optical coupler 38 with respect to one another such that each of the fiber cores A1, A2 and A3 of the fiber sensor 12 is in optical communication with one of the optical channels C1, C2, C3 in a one-to-one relationship. It is to be noted again, that upon making the connection of the fiber sensor connection end 30 to the optical coupler 38 does not require that the fiber cores A1, A2 and A3 are in optical communication with the correct of ones of the optical channels C1, C2 and C3 of the optical coupler 38, because the correct optical connection will be established by the further steps S2, S3, S4A/S4B of the method as described above.

When step S1 comprises positioning the fiber sensor connection end 30 and/or the optical coupler 38 with respect to one another such that each of the fiber cores A1, A2 and A3 of the fiber sensor 12 is in optical communication with one of the optical channels C1, C2, C3 of the optical coupler 38 in a one-to-one relationship, then further embodiments provide that step S2 comprises measuring an optical response of each of the fiber cores A1, A2, A3 by optically interrogating the fiber cores A1, A2, A3, and step S3 further comprises identifying each of the fiber cores A1, A2, A3 among the fiber cores A1, A2, A3 of the fiber sensor 12. Then, step S4A may comprise reassigning the calibration data sets to the optical channels C1, C2, C3 so that the identified fiber cores A1, A2, A3 match with the calibration data sets, and step S4B may comprise repositioning the fiber sensor connection end 30 and/or the optical coupler 38 such that the fiber cores A1, A2, A3 matching with the calibration data sets are in optical communication with the optical channels C1, C2, C3 in the relationship A1-C1, A2-C2, A3-C3, while the calibration data set of fiber core A1 is assigned to channel C1, etc.

In further embodiments, step S1 may further comprise, when making the connection of the fiber sensor connection end 30 with the optical coupler 38, optically interrogating, in the above example, the optical channel C1, and positioning, in particular rotating about the longitudinal center axis (central core), the fiber sensor connection end 30 and/or the optical coupler 38 until a strength of an optical response signal from the interrogated fiber core, here fiber core A2, is maximal. This allows for a fine-tuned rotational alignment of the fiber sensor connection end 30 with respect to the optical coupler 38. Steps S2 to S4A/S4B can be then performed as described above. In further embodiments, a further step S5 in FIG. 6 is provided which comprises optically interrogating each of the fiber sensor cores and positioning the fiber sensor connection end and/or the optical coupler until a strength of an optical response signal from each of the fiber cores A1, A2 and A3 is maximal. This further allows for a fine-tuned rotational alignment of the fiber sensor connector end 30 and the optical coupler 38 with respect to all fiber cores A1, A2 and A3 and also of fiber core A4. Step S5 may also be carried out in step S1.

Finding maximum signal strength may require another feedback loop to fine-tune the rotational alignment of the fiber sensor connection end 30 and the optical coupler 38. The signal used for this alignment may for example be the Bragg or Rayleigh back scattering signal from the fiber sensor or fiber sensors A1, A2 and A3.

In the following, embodiments will be described, how the measurement in step S2 can be used to identify the fiber cores A1, A2, A3 of the fiber sensor 12. It is to be noted that the embodiments to be described in the following can be used individually or can be combined to potentially improve the accuracy of the fiber core identification.

One of the embodiments for identifying the fiber cores A1, A2 and A3 of the fiber sensor 12 uses characteristics of fiber Bragg gratings written over the length of the fiber cores A1, A2, A3. A fiber Bragg grating is a periodic modulation of the index of refraction of a fiber core. Although the fiber Bragg gratings in each of the outer cores A1, A2, A3 should be nominally the same, the manufacturing process induces small differences between them. Some of these differences, such as shadowing dips or small irregularities in grating strength, are visible in the reflected spatial intensity profile, i.e. the absolute values of the state-file, which in turn is the spatially resolved scattering profile of the interrogated fiber core. Even when the fiber sensor 12 is bent, the spatial intensity profile hardly changes. Therefore, the reflected spatial intensity profile is well suited to identify the cores A1, A2 and A3.

In order to verify that using the spatial intensity profile is suitable for identifying the single fiber cores A1, A2 and A3 in the fiber sensor 12, a test has been performed using N=95 fiber sensors. For each of the fiber sensors, the spatial intensity profiles of all fiber cores have been measured, while the fiber sensor was in a shape that had significantly more curvature than the reference measurement taken during the calibration from which the calibration data sets of the fiber cores of this fiber sensor have been obtained. Then, the cross-correlation for all fiber cores of these measurements with the reference measurements from the calibration data sets have been calculated.

Figure 7:
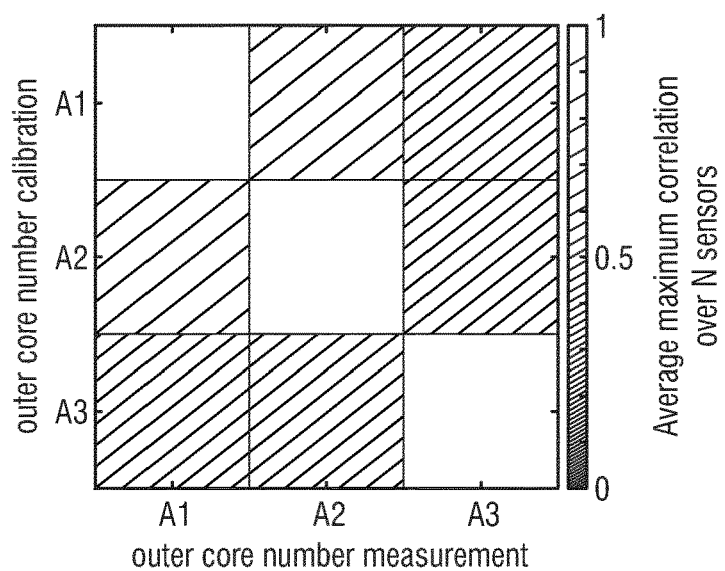
FIG. 7 shows a diagram illustrating the efficacy of identifying the fiber cores of a sensor fiber for a plurality of fiber sensors by using the different optical behavior of fiber Bragg gratings in the fiber cores.
Figure 8:
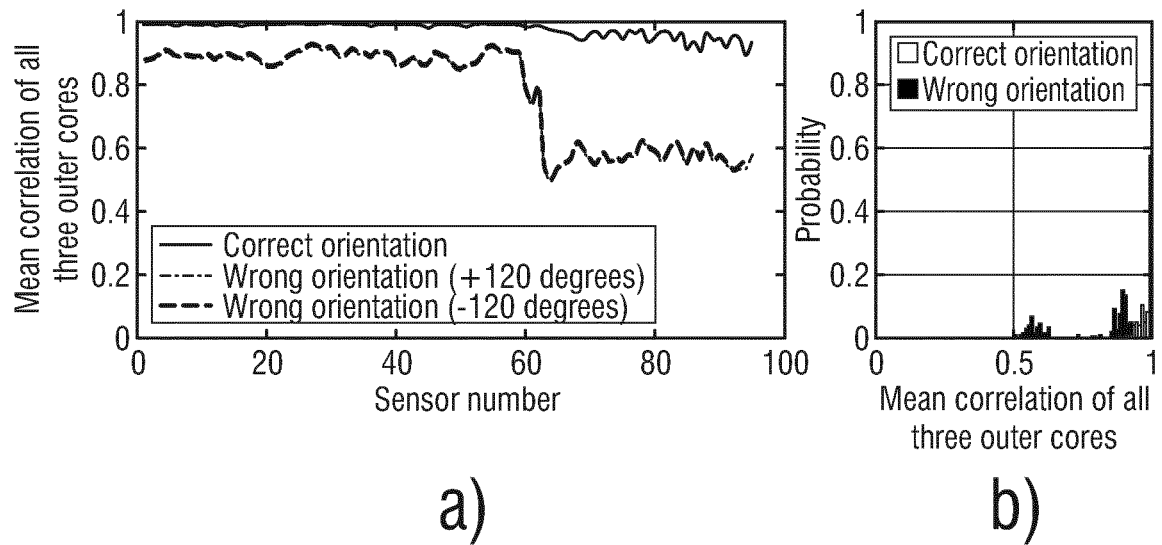
FIGS. 8a) and b) show graphs further illustrating the efficacy of identifying the fiber cores of a fiber sensor for a plurality of fiber sensors based on the different optical behavior of fiber Bragg gratings of the fiber cores.

The results of the correlations are shown in FIG. 7 and FIGS. 8a) and 8b).

FIG. 7 shows a diagram in which the vertical axis refers to the intensity profiles using the calibration data sets of the outer fiber cores A1, A2, A3, and in which the horizontal axis refers to the modulus, i.e. the absolute values of the state-file taken during the measurement, e.g. in step S2. The right column illustrates the average maximum correlation over the N=95 fiber sensors in a scale from 0 to 1. The less dense the hatchings in the quadrants in FIG. 7 are the higher is the correlation. As can be taken from FIG. 7, the highest or maximum correlation is obtained when the fiber core is connected to the optical channel to which the calibration data set of that fiber core is assigned.

FIG. 8a) shows graphs of the mean correlation of all three outer cores A1, A2, A3 along the vertical axis for the N=95 fiber sensors. The solid line shows a graph for the case that the fiber sensor connection end 30 was in the correct orientation with respect to the coupler 38 which means that fiber core A1 was connected to optical channel C1, fiber core A2 to optical channel C2, and fiber core A3 to optical channel C3, and the calibration data set of fiber core A1 was assigned to optical channel C1, the calibration data set of fiber core A2 was assigned to optical channel C2, and the calibration data set of fiber core A3 was assigned to optical channel C3. The other two graphs in FIG. 8a) instead show a wrong orientation of the fiber sensor connection end 30 with respect to the optical coupler 38, where the fiber sensor connection end 30 was mis-oriented by +120 degrees in one case and −120 degrees in the other case. As can be taken from FIG. 8a), for all of the 95 fiber sensors the mean correlation of all three outer cores was maximal in the correct orientation of the fiber sensor connection end 30 with respect to the optical coupler 38. In other words, one can clearly see that there is a significantly higher correlation when the same outer cores in the measurement and in the calibration are used compared to different outer cores. When all permutations of the calibration data with respect to the measurements were tried, and when the permutation with highest correlation was picked to identify the fiber cores, the outer cores were correctly identified with a yield of 100%, as illustrated in FIG. 8b).

In another embodiment, the optical response measured in step S2 is used in a different way than in the embodiment before, in order to identify the fiber cores A1, A2, A3 of the fiber sensor 12. This embodiment of evaluating the measured state-file, i.e. the spatially resolved scattering profiles of the fiber cores A1, A2, A3 makes use of the sensor geometry of the fiber sensor 12. The background is that the geometry of a fiber sensor is never perfect and small differences between the different fiber cores exist. Therefore, when the calibration data sets of the outer cores A1, A2, A3 are interchanged in the measurement in step S2, the reconstruction of the shape of the fiber sensor 12 will show distinct errors. At places where there is a curvature or twist in the fiber sensor 12, oscillations will appear on the twist calculated from the state-file, due to slight differences in the positions of the outer cores A1, A2, A3 with respect to the mechanical center of the fiber sensor 12, which is the central fiber core A4. These oscillations have a frequency corresponding to the twist rate of the fiber sensor 12 and can therefore be detected relatively easily.

Figure 9:
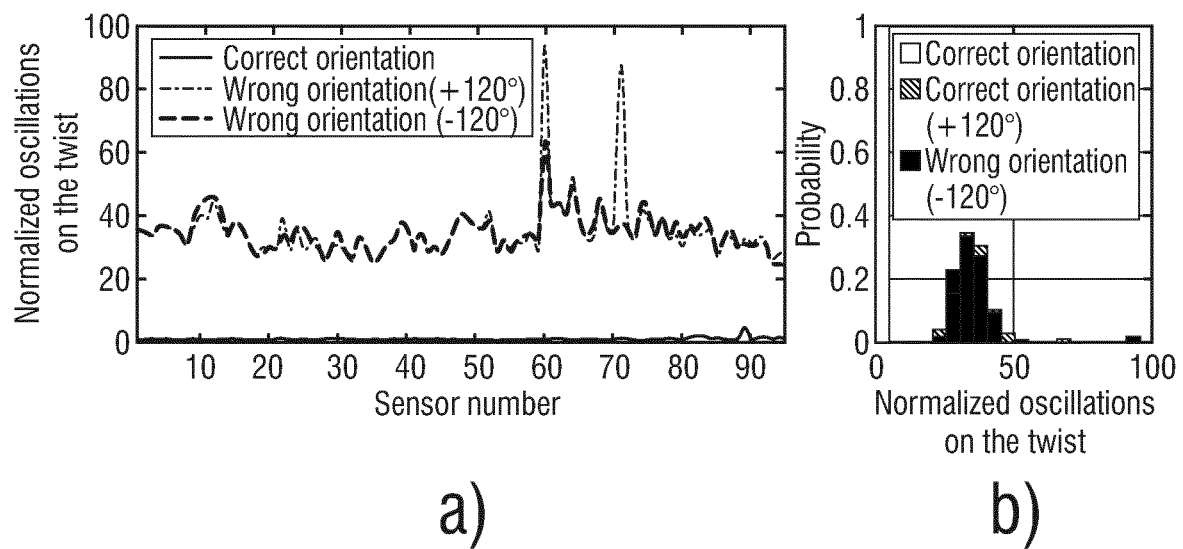
FIGS. 9a) and b) show graphs illustrating the efficacy of identifying the fiber cores of a fiber sensor for a plurality of fiber sensors based fiber sensor geometry.

In a test for verifying this embodiment, a total of N=95 different sensor fibers were tested, and it was tried to analyze the measurements with all three possible permutations that could be caused by attaching the fiber sensor 12 in correct and wrong orientations to the optical coupler 38. Each time the twist was calculated and oscillations were identified corresponding to the twist rate. The results are plotted in FIG. 9a). FIG. 9a) shows the normalized oscillations on the twist of the reconstructed shape at the spatial frequency corresponding to the internal twist rate of the interrogated fiber sensor. The oscillations are normalized to the average oscillations seen in the correct orientation of the connection of the fiber sensor with respect to the optical coupler. The three possible permutations were tested. In the first correct orientation, the calibration data sets of outer fiber cores A1, A2, and A3 is used on the measurement of fiber cores A1, A2, and A3 respectively. In the second (wrong) orientation (correct orientation plus 120 degrees), the calibration data sets of the outer fiber cores A2, A3, and A1 were used on the measurement of fiber cores A1, A2, and A3 respectively. In the last (wrong) orientation (correct orientation minus 120 degrees), the calibration data sets of outer fiber cores A3, A1 and A2 were used on the measurement of fiber cores A1, A2, and A3 respectively. When one of the wrong orientations is used, an increase in oscillations can be seen. On the other hand, when the proper calibration data sets are used (correct orientation), the oscillations are almost completely absent. When taking for each of the tested fiber sensors the orientation that results in the lowest oscillation, the test revealed that this embodiment is perfectly suited to identify the fiber cores with a yield of 100% as can be taken from the left column in FIG. 9b).

In further embodiments, the connection end 30 of the fiber sensor 12 may have a mark that may help to align the fiber sensor 12 approximately in the right orientation straight away. Such a mark may help to render the alignment procedure in step S1 faster and more robust. The mark may have no or no significant physical size compared to the size of the connection end 30 and may itself not give perfect alignment, but only provide guidance to a proper alignment. The mark will have to be interpreted and active alignment (rotation) is required. Such marks may be visible marks, for example a thin line of different color or reflection, written on the fiber sensor 12 with paint, ink or by local alteration of the material by a laser. Other embodiments of marks can comprise a magnetic field due to magnetization of the proximal part of the fiber sensor 12, for example at right angles to the longitudinal axis of the fiber sensor 12.

With reference again to FIG. 1, the optical shape sensing system 10 may comprise a system 100 for optically connecting the optical fiber sensor 12 to the optical shape sensing console 21 according to a method as described above. The system 100 comprises a calibration data module 28 as described above which is configured to have stored in a number of single calibration data sets indicative of individual optical properties of the single fiber cores A1, A2, A3, A4 of the fiber sensor 12, the calibration data sets being assigned to the single optical channels C1 (24a), C2 (24b), C3 (24c), C4 (24d) upon connection of the fiber sensor 12 to the shape sensing console 21. The system 100 further comprises a measuring module 52 configured to carry out shape sensing measurements on the fiber sensor 12 when connected to the shape sensing console 21. The calibration data module 28 and the measuring module 52 may be modules an optical shape sensing system conventionally has. The system 100 further comprises an identifying module 54 configured to identify at least the outer fiber cores A1 (14), A2 (18), A3 (20) of the fiber sensor 12 as described above.

The system 100 further may comprise a re-assigning module 56 configured to reassign the calibration data sets among the optical channels 24a, 24b, 24c, 24d. Further, the system 100 may comprise a repositioning module 58 configured to reposition the fiber sensor connection end 30 and/or the optical coupler 32 or 38 such that the fiber cores 14, 18, 20 are optically connected to the optical channels 24a, 24b, 24c, 24d in the correct orientation. The repositioning module may control an actuator for rotating at least one of the fiber sensor connection end 30 and the optical coupler 32/38.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program comprising program code means for causing a computer to carry out a method as described herein may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope of the claims.

The invention claimed is:

1. Method of optically connecting an optical fiber sensor to an optical shape sensing console, the optical shape sensing console having a number of single optical channels, the optical fiber sensor having a number of single fiber cores angularly spaced with respect to one another around a longitudinal center axis of the fiber sensor and a fiber sensor connection end for connection to an optical coupler connected to the shape sensing console, the optical coupler having the optical channels arranged for optical connection with the fiber cores, a number of single calibration data sets indicative of individual optical properties of the single fiber cores being assigned to the single optical channels, the method comprising the steps:
  i) connecting the fiber sensor connection end to the optical coupler such that a first fiber core of the fiber cores is in optical communication with a first optical channel of the optical channels,
  ii) measuring an optical response of the first fiber core by optically interrogating the first fiber core while a first calibration data set of the calibration data sets is assigned to the first optical channel,
  iii) identifying the first fiber core among the fiber cores of the fiber sensor on the basis of the measured optical response of the first fiber core and the calibration data sets of the fiber sensor, and
  iv) if the first fiber core is identified as not matching with the first calibration data set used in measuring the optical response, then
    iva) reassigning a second calibration data set of the calibration data sets, which matches with the identified first fiber core, to the first optical channel, or
    ivb) repositioning the fiber sensor connection end and/or the optical coupler such that a second fiber core matching with the first calibration data set is in optical communication with the first optical channel.

2. Method of claim 1, wherein step i) comprises positioning the fiber sensor connection end and/or the optical coupler with respect to one another such that each of the fiber cores is in optical communication with one of the optical channels in a one-to-one relationship.

3. Method of claim 2, wherein step ii) comprises measuring an optical response of each of the fiber cores by optically interrogating the fiber cores, and step iii) comprises identifying each of the fiber cores among the fiber cores of the fiber sensor.

4. Method of claim 3, wherein step iva) comprises reassigning the calibration data sets to the optical channels so that the identified fiber cores match with the calibration data sets, or step ivb) comprises repositioning the fiber sensor connection end and/or the optical coupler such that the fiber cores matching with the calibration data sets are in optical communication with the optical channels.

5. Method of claim 1, wherein step i) further comprises optically interrogating the first optical channel and positioning the fiber sensor connection end and/or the optical coupler until a strength of an optical response signal from the first fiber core is maximal.

6. Method of claim 1, further comprising optically interrogating each of the fiber sensor cores and positioning the fiber sensor connection end and/or the optical coupler until a strength of an optical response signal from each of the fiber cores is maximal.

7. Method of claim 1, wherein the measured optical response in step ii) includes a spatially resolved scattering profile of the first fiber core.

8. Method of claim 7, wherein the fiber cores have fiber Bragg gratings as scattering structures, and step iii) comprises identifying the first fiber core by using a spatial intensity profile obtained from the spatially resolved scattering profile.

9. Method of claim 8, wherein step iii) comprises calculating a cross-correlation of the measured optical response with the calibration data sets of the fiber cores.

10. Method of claim 7, wherein step iii) comprises calculating a twist or curvature in the fiber sensor from the spatially resolved scattering profile and identifying the first fiber core based on oscillations in the calculated twist or curvature.

11. Method of claim 1, wherein the calibration data sets include spatially resolved scattering profiles or spatial intensity profiles thereof of the fiber cores, which have been obtained from reference measurements on the fiber cores.

12. Method of claim 1, wherein the optical coupler is arranged on a patch cord connected to the shape sensing console or is arranged on the shape sensing console.

13. System for optically connecting an optical fiber sensor to an optical shape sensing console, the optical shape sensing console having a number of single optical channels, the optical fiber sensor having a number of single fiber cores angularly spaced with respect to one another around a longitudinal center axis of the fiber sensor and a fiber sensor connection end (30) for connection to an optical coupler connected to the shape sensing console, the optical coupler having the optical channels arranged for optical connection with the fiber cores, the system comprising a calibration data module configured to have stored a number of single calibration data sets indicative of individual optical properties of the single fiber cores, the calibration data sets being assigned to the single optical channels, a measuring module configured to measure an optical response of a first fiber core of the fiber cores connected to a first optical channel by optically interrogating the first fiber core while a first calibration data set of the calibration data sets is assigned to the first optical channel, an identifying module configured to identify the first fiber core among the fiber cores of the fiber sensor on the basis of the measured optical response of the first fiber core and the calibration data sets of the fiber sensor, the system further comprising at least one of the following:

a) a reassigning module configured to reassign a second calibration data set of the calibration data sets, which matches with the identified first fiber core, to the first optical channel, b) a repositioning module configured to reposition the fiber sensor connection end and/or the optical coupler such that a second fiber core matching with the first calibration data set, is in optical communication with the first optical channel.

14. An optical shape sensing system, comprising
an optical shape sensing console, the optical shape sensing console having a number of single optical channels,
at least one optical fiber sensor having a number of single fiber cores angularly spaced with respect to one another around a longitudinal center axis of the fiber sensor and a fiber sensor connection end,
an optical coupler for connecting the optical fiber sensor to the optical shape sensing console, the optical coupler having the optical channels arranged for optical connection with the fiber cores, and
the system of claim 13 for optically connecting the optical fiber sensor to the optical shape sensing console.

15. Computer program comprising program code means for causing a computer to carry out the steps of the method as claimed in claim 1, when said computer program is carried out on a computer.

* * * * *